United States Patent
Kamalasanan et al.

(10) Patent No.: US 9,368,734 B2
(45) Date of Patent: Jun. 14, 2016

(54) LITHIUM METAL QUINOLATES AND PROCESS FOR PREPARATION THEREOF AS GOOD EMITTING, INTERFACE MATERIALS AS WELL AS N-TYPE DOPENT FOR ORGANIC ELECTRONIC DEVICES

(75) Inventors: Modeeparampil Narayanan Kamalasanan, New Delhi (IN); Ritu Srivastava, New Delhi (IN); Amit Kumar, New Delhi (IN); Ishwar Singh, Rohtak (IN); Sandeep Kumar Dhawan, New Delhi (IN); Sukhwant Singh Bawa, New Delhi (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 721 days.

(21) Appl. No.: 13/529,815

(22) Filed: Jun. 21, 2012

(65) Prior Publication Data

US 2013/0015431 A1    Jan. 17, 2013

(30) Foreign Application Priority Data

Jun. 21, 2011    (IN) .......................... 1746/DEL/2011

(51) Int. Cl.
| | |
|---|---|
| *H01L 51/54* | (2006.01) |
| *H01L 51/00* | (2006.01) |
| *C07D 215/30* | (2006.01) |
| *C09K 11/06* | (2006.01) |
| *H05B 33/14* | (2006.01) |
| *H01L 51/50* | (2006.01) |

(52) U.S. Cl.
CPC .......... *H01L 51/0077* (2013.01); *C07D 215/30* (2013.01); *C09K 11/06* (2013.01); *H05B 33/14* (2013.01); *C09K 2211/1029* (2013.01); *C09K 2211/181* (2013.01); *H01L 51/5012* (2013.01); *H01L 51/5076* (2013.01); *H01L 51/5092* (2013.01); *H01L 2251/558* (2013.01)

(58) Field of Classification Search
None
See application file for complete search history.

(56) References Cited

U.S. PATENT DOCUMENTS

| | | | | |
|---|---|---|---|---|
| 2002/0027416 | A1* | 3/2002 | Kim et al. ...................... | 313/506 |
| 2006/0286405 | A1* | 12/2006 | Begley et al. ................. | 428/690 |
| 2010/0289009 | A1* | 11/2010 | Ganeshamurugan et al. .. | 257/40 |

OTHER PUBLICATIONS

Sun et al. "Sodium-Quinolate Complexes as Efficient Electron Injection Materials for Organic Light-Emitting Diode Devices" J. Phys. Chem. C 2011, 115, 2433-2438. Date of publication: Jan. 6, 2011.*

* cited by examiner

Primary Examiner — Andrew K Bohaty
(74) Attorney, Agent, or Firm — John P. White; Cooper & Dunham LLP (57) ABSTRACT

Invention relates to a single step preparation of alkali metal quinolate of general formula 1

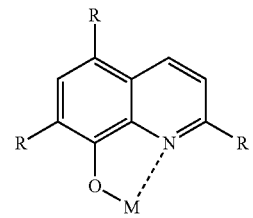

wherein
M=Lithium, sodium or potassium;
R=H, alkyl (C1-C6), alkoxy, aryl, aryloxy, amino, amido or halogen (Cl, F, Br, I)
which is substituted or unsubstituted with direct reaction of metal with 8-hydroxyquinoline. Substituted 8-hydroxyquinoline optionally have at least one substituent selected from the group consisting of alkyl, alkoxy, aryl, aryloxy, amino, amido at 2, 5 or 7 position. Halogen substituted 8-hydroxyquinolates are also prepared from this method in the yield of 90-95% from polar solvents like acetonitrile. These complexes are useful as light emitting and electron injecting materials in organic electronic devices. Also the doping of these materials in electron transport materials improves their electron mobility.

15 Claims, 8 Drawing Sheets

LITHIUM METAL QUINOLATES AND PROCESS FOR PREPARATION THEREOF AS GOOD EMITTING, INTERFACE MATERIALS AS WELL AS N-TYPE DOPENT FOR ORGANIC ELECTRONIC DEVICES

FIELD OF THE INVENTION

The present invention relates to an improved process for the preparation of compounds of general formula 1 wherein
M=Lithium, sodium or potassium;
R=H, alkyl (C1-C6), alkoxy, aryl, aryloxy, amino, amido or halogen (Cl, F, Br, I)

More particularly, the present invention relates to a single step preparation of alkali metal quinolate of general formula 1 which is substituted or unsubstituted with direct reaction of metal with 8-hydroxyquinoline. Substituted 8-hydroxyquinoline optionally have at least one substituent selected from the group consisting of alkyl, alkoxy, aryl, aryloxy, amino, amido at 2, 5 or 7 position. Halogen substituted 8-hydroxyquinolates are also prepared from this method in the yield of 90-95% from polar solvents like acetonitrile. The present invention more particularly relates to the use of these complexes as light emitting and electron injecting materials in organic electronic devices. Also the doping of these materials in electron transport materials improves their electron mobility.

BACKGROUND OF THE INVENTION

Use of organic materials in electronic devices makes such devices relatively inexpensive, easy process ability and cost effective over inorganic materials. In addition, the inherent property of organic materials, such as their flexibility, may make them well suited for particular applications such as fabrication on a flexible substrate. Examples of organic optoelectronic devices include organic light emitting devices (OLEDs), organic phototransistors, organic photovoltaic cells and organic photodetectors. For OLEDs, the organic materials may have performance advantages over conventional materials. For example, at which an organic emissive layer emits light may generally be readily tuned with appropriate selection of metal ion, ligands modification (introduction of electron donating or electron withdrawing moiety), increasing chain length or by appropriate dopants etc.

The term 'organic' includes small molecule organic materials as well as polymeric materials that may be used to fabricate organic electronic device such as OLEDs. Metal complexes having organic ligand part also fall in the category of small molecule organic materials. Small molecules may actually be quite large and may include some repeated unit. For example, central metal having a long chain alkyl group as a substituent in the ligand does not remove a molecule from the 'small molecule' class. Such metal complexes may also be incorporated into polymers disclosed in U.S. Pat. No. 5,066,695. Small molecule may also serve as the metal centered core moiety of a dendrimer, which consists of a series of chemical shells built on the core moiety. The core moiety of a dendrimer may be a fluorescent or phosphorescent small molecular emitter. A dendrimer may be a small molecule and it is believed that all dendrimers currently used in the field of OLEDs are small molecules.

Although lithium metal quinolates are known complexes but so far as the previous methods of preparation of Liq are concerned, the complex is made by reacting the alkyllithiums viz. n-butyllithium, 1-hexyllithium, 2-ethylhexyllithium, 1-octyllithium etc. with 8-hydroxyquinoline in an inert atmosphere. Alkyllithiums are quite difficult to prepare as described in U.S. Pat. Nos. 3,122,592, 3,293,313, 3,420,903, 5,332,533, 5,626,798, 5,663,398, 7,005,083, 20040251562, where lithium metal is dispersed to a particle size of 300 micron, washed with hexane and pentane, drying in argon and then lithium is transferred through a tube to a Morton Cleaved 3-nacked flask equipped with a reflux condenser, Y-tube for addition, pressure-equalizing addition funnel, stirring shaft with teflon blade, stirring motor, a thermometer probe and means for maintaining an inert atmosphere in the reactor. The lithium-hexane mixture is heated to reflux (dry ice/hexane in condenser) and dropwise feed of alkylchloride. The process needs continuous attention and reaction heat is controlled strictly by the rate of reflux. Hence the synthesis of lithium quinolate from alkyl lithium is quite difficult, also the handling of alkyl lithium are quite difficult and reaction of these require special attention Operating voltage is a key feature of an organic electroluminescence device, in order to reduce the operating voltage of the device, the injection of electrons and holes should be balanced. It is needed to improve electron injection ability. The use of low work function metal as a cathode can improve electron injecting ability. However, the low work function metals are too active and opt to react with oxygen and water. Another method for improving electron injecting ability is to add an electron injecting layer formed of an inorganic compound layer between said cathode and an organic layer as described in U.S. Pat. Nos. 6,172,459, 6,023,073, 6,013,384, 5,989,737 etc. It has been proved in practice that LiF/Al is a cathode structure having excellent electron injecting ability, which is widely used in organic electronic devices. However, the major problem with these materials is that upon slightly increasing the thickness of these materials from required one, they form highly insulating contact. Different metal complexes are also used as electron injecting materials.

In organic electronic devices particularly in OLEDs there are various organic layers are present in between the electrodes. In layers comprising organic materials and metal complexes, the number of charge carriers may be very low, significantly limiting the conductivity of the layer. A particular solution of this problem involves doping the film with redox active dopents, leading to controlled oxidation or reduction of the carrier transporter, creating finite charge carriers. $Alq_3$, phenanthrolines and other electron transporting materials have been successfully doped with Li to significantly enhance their conductivity. [(a) 'Lithium doping of semiconducting organic charge transport materials.' Parthasarathy G., Shen C., Kahn A., Forrest S. R. J. Appl. Phys. (2001), 89(9), 4986-4992. (b) 'Low-voltage inverted transparent vacuum deposited organic light emitting diodes using electrical doping.' Zhou, X.; Pfeiffer, M.; Huang, J. S.; Blochwitz-Nimoth, J.; Qin, D. S.; Werner, A.; Drechsel, J.; Maennig, B.; Leo, K. Appl. Phys. Lett. (2002), 81(5), 922-924. (c) 'Efficient multilayer organic light emitting diode' Liu, Z.; Pinto, J.; Soares, J.; Pereira, E. Synthetic Metals (2001), 122(1), 177-179. (d) Electron structure of tris(8-hydroxyquinoline)aluminum thin film in the pristine and reduced states.' Johansson, N.; Osada, T.; Stafstrom, S.; Salaneck, W. R.; Parente, V.; Dos Santos, D. A.; Crispin, X.; Bredas, J. L. J. Chem. Phys. (1999), 111(5), 2157-2163. (e) 'Bright organic electroluminescent devices having a metal doped electron-injecting layer.' Kido, J.; Matsumoto, T. Appl. Phys. Lett. (1998), 73(20), 2866-2868. (f) 'Improved efficiency of organic light emitting devices employing bathocuproine doped in the electron-transporting layer.' Wu, Z.; Yang, H.; Duan, Tu; Xie, W.; Liu, S.; Zhao, Yi. Semicond. Sci. Technol. (2003), 18, L49-L52.]. However, there are two potential drawback of Li doping is that the number of free charge carriers generated by lithium doping is far less then the amount of Li that doped into the film(carriers/Li<10%). The low yield of free carriers is thought to be due to the formation of charge transfer complexes, or tightly bound ion pairs. ['Investigation of interface formation between calcium and tris(8-hydroxyquinoline)aluminum.' Choong, V. E.; Mason, M. G.; Tang, C. W.; Gao, Y. Appl. Phys. Lett. (1998), 71(21), 2689-2691]. A second problem of Li doping is that Li may be highly mobile, readily diffuse throughout the device and markedly degrade the device performance due to the formation of trapping or quenching sites. Clearly the problem with Li doping are related to its high charge density and small size.

OBJECTS OF THE INVENTION

The main object of the present invention is to provide an improved process for the preparation of compounds of alkali metal with 8-hydroxyquinoline and substituted 8-hydroxyquinoline. More particularly, the present invention provide a single step preparation of electroluminescent lithium quinolate which is substituted or unsubstituted comprising direct reaction of lithium metal with 8-hydroxyquinoline, the 8-hydroxyquinoline optionally having at least one substituent selected from the group consisting of alkyl, alkoxy, aryl, alkoxy, amino, amido.

Another object of the invention is to synthesize halogen substituted 8-hydroxyquinolates, which are also prepared from this method in the yield of 90-95% from polar solvents like acetonitrile.

Yet another object of the invention is to minimizing the reaction time.

Yet another object of the invention is to use the prepared metal complexes as emissive materials for organic light emitting diodes.

Still another object of the invention is to use these metal complexes as electron injecting materials.

Still another object of the invention is to improve the transport property of electron transport materials by the small doping of these materials in it.

ABBREVIATIONS USED

OLED—Organic light emitting diode
Alq$_3$—Tris(8-hydroxyquinolinato)aluminum(III)
ITO—Indium tin oxide
α-NPD-N,N'-diphenyl-N,N'-bis(1-naphthyl)-1,1'-biphenyl-4,4'-diamine
Ir(ppy)$_3$—tris(2-phenylpridine)iridium
CBP—4,4-N,N'-dicarbazole-biphenyl
BCP—2,9-dimethyl-4,7-diphenyl-1,10-phenanthroline
LiF—Lithium fluoride
Al—Aluminum
Cl$_1$—5-chloro-8-hydroxyquinolinatolithium(I)
Cl$_2$—5,7-dichloro-8-hydroxyquinolinatolithium(I)
M$_2$—5,7-dimethyl-8-hydroxyquinolinatolithium(I)
HTL—Hole transport layer
ETL—Electron transport layer
EIL—Electron injection layer

SUMMARY OF THE INVENTION

Accordingly, present invention provides a process for the preparation of compound of general formula 1 wherein
M=Lithium, sodium or potassium;
R=H, alkyl (C1-C6), alkoxy, aryl, aryloxy, amino, amido or halogen (Cl, F, Br, I)
and the said process comprising the steps of:
  i. dissolving substituted 8-hydroxyquinoline of formula 1 and fresh scratched metal in 1:1 molar ratio in polar solvent with continuous stirring for period in the range of 20 to 25 min to obtain a solution;

Formula 1 wherein
R=H, alkyl (C1-C6), alkoxy, aryl, aryloxy, amino, amido or halogen (Cl, F, Br, I)
  ii. filtering the solution as obtained in step (i), drying in vacuum at temperature in the range of 100 to 120° C. for period in the range of 10 to 12 hrs followed by purification by vacuum sublimation to obtain pure compound of general formula 1.

In an embodiment of the present invention, metal used in step (i) is selected from the group consisting of Lithium, sodium or potassium.

In another embodiment of the present invention, the polar solvent used in step (i) is selected from the group consisting of acetonitrile, methanol, ethanol, propanol, dichloromethane.

In yet another embodiment of the present invention, the yield of compound of general formula 1 is in the range of 90 to 95%.

In yet another embodiment of the present invention, wherein representative compounds of general formula 1 comprising following compounds:

Compound 1

Compound 2

Compound 3

Compound 4

Compound 5

Compound 6

Compound 7

Compound 8

In yet another embodiment of the present invention, an organic light emitting device comprising among other layers an electron injecting layer formed by compound of general formula 1 wherein M is selected from the group consisting of Lithium, sodium or potassium; R is selected from the group consisting of H, alkoxy, aryl, aryloxy, amino, amido or halogen (Cl, F, Br, I) having at least one substituent other than hydrogen.

In yet another embodiment of the present invention, in an organic light emitting device, compound of general formula 1 are used as n-dopant in electron transport layer.

In yet another embodiment of the present invention, n-dopants are in the range of 10 to 30%.

In yet another embodiment of the present invention, thickness of the said electron injecting layer is in the range of 1 to 2 nm.

In yet another embodiment of the present invention, thickness of the said organic emissive layer is in the range of 30 to 35 nm.

In yet another embodiment of the present invention, an organic light emitting device comprising:
  i. a substrate layer;
  ii. an anode layer superimposed on substrate layer;
  iii. a hole transport layer deposited on the anode layer;
  iv. an organic emissive layer covering the hole transport layer;
  v. an electron transport layer covering the organic emissive layer;
  vi. an electron injection layer covering the electron transport layer;
  vii. a cathode superimposed over the electron injection layer.

In yet another embodiment of the present invention, substrate layer is composed of transparent glass.

In yet another embodiment of the present invention, anode layer is composed of indium tin oxide.

DETAILED DESCRIPTION OF THE INVENTION

The present invention relates to simplify the synthesis method of alkali metal quinolates. Lithium quinolates are good photoluminescent and electroluminescent materials and emits light in blue region of the visible spectrum. Color tuning is also done by introducing electron donating and electron withdrawing group in the legend. Lithium quinolates are also form good electron injecting contact with low work function metal electrodes. Also the small doping of these materials in electron transport materials improves their electron mobality.

Emitting and interface properties of lithium quinolate complexes are studied in an article by Christoph Schmitz, Hans-Werner Schmidt, and Mukundan Thelakkat in Chem. Mater. 2000, 12, 3012-3019. Lithium metal complexes with substituted quinolates are also synthesized by this simplified method. Emitting, interface and effect of doping of these materials in common electron transporting material are also studied.

The injection properties of the materials were compared with the well established electron injecting material (LiF) and with unsubstituted lithiumquinolate (8-hydroxyquimolinatolithium) comprising:
  i. An electrically conducting substrate,
  ii. Device was fabricated by depositing the different layers with vacuum deposition process;
  iii. Device having 1 nm LiF as an electron injecting material was compared with the devices structure ITO/α-NPD(30 nm)/Alq$_3$(35 nm)/substituted quinolates (Xnm)/Al having new materials with different thickness (1 nm to 2 nm) as electron injecting materials.

The present disclosure describes in which a buffer layer of the substituted quinolates layer will be forming a highly injecting contact then lithiumfluoride and unsubstituted lithiumquinolate with aluminium.

Here the improved injection as compared to lithiumfluoride and unsubstituted lithiumquinolate from low work function electrode like aluminum is because of the electron donating/withdrawing substutuents present on the ligand (phenoxide or prydine ring).

Doping of substituted metal quinolate increases the electrical conductivity of the common electron transporting material (e.g. Alq$_3$), studied using the ETL doped with newly synthesized materials. Organic LED devices were fabricated comprising:
  i. An electrically conducting substrate,
  ii. Device was fabricated by depositing the different layers with vacuum deposition process,
  iii. Device having undoped Alq$_3$ as electron transporting material having structure ITO/α-NPD(30 nm)/5% Ir(ppy)$_3$ in CBP(35 nm)/BCP(6 nm)/Alq$_3$(28 nm)/LiF(1 nm)/Al was compared with substituted metal quinolate doped Alq$_3$ as electron transporting material having device structure ITO/α-NPD(30 nm)/5% Ir(ppy)$_3$ in CBP(35 nm)/BCP(6 nm)/x % substituted quinolates doped Alq$_3$(28 nm)/LiF(1 nm)/Al, Doping concentration of materials was varied from 0% to 30% and compared with device having undoped Alq$_3$ as electron transporting material device. Opto-electronic properties of the devices were recorded at room temperature (25 to 35° C.). In the devices as described in claim 7 the luminescence, current efficiency and power efficiency of the doped Alq$_3$ was found to be greater then undoped Alq$_3$. 20% doping of Alq$_3$ with newly synthesized halogen substituted complex give best result.

Since lithiumquinolates molecules have very similar electronic properties as Alq$_3$ and the energy level mismatch between the two molecules is minimal. Since lithiumquinolates are more ordered than Alq$_3$, the addition of the correction factor is likely to place the effective lithiumquinolates electron affinity lower than that of Alq$_3$. As a result the doping of lithiumquinolates into Alq$_3$ leads to the easy electron transfer from the LUMO of Alq$_3$ to the LUMO of lithiumquinolates which is energetically favorable.

The present disclosure also describes in which device using substituted quinolates doped layer of Alq$_3$ as electron transport layer shows better device efficiencies in terms of current efficiency and power efficiency then undoped Alq$_3$ electron transport layer.

Here the improved efficiencies as compared to undoped layer is because of the more ordered structure and electron donating/withdrawing substutuents present on the ligand (phenoxide or prydine ring).

Figure 1:
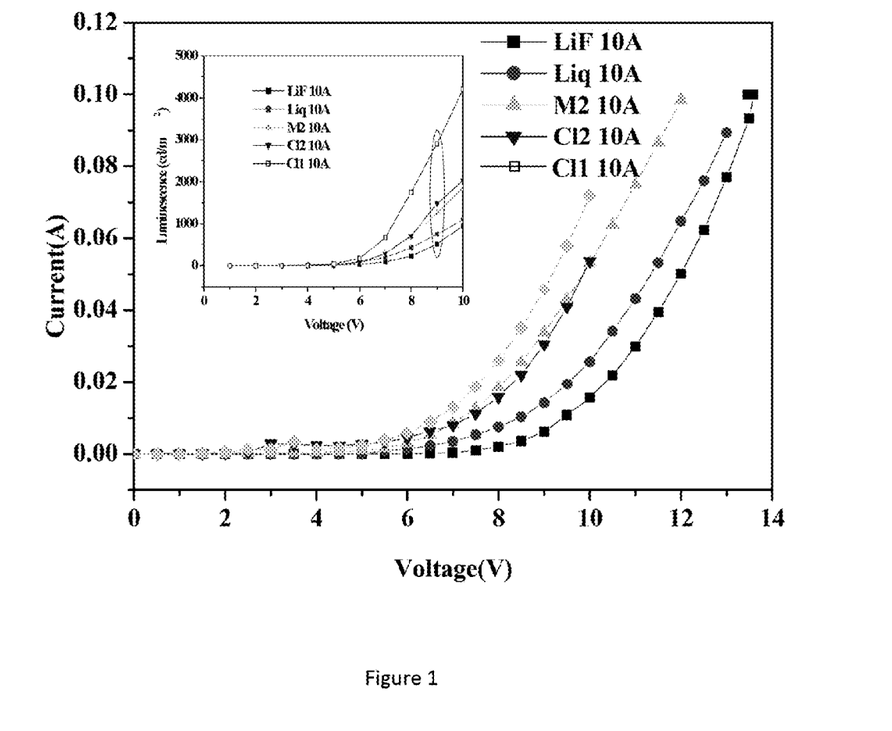
FIG. 1 is a graph illustrating comparative voltage v. current and comparative voltage v. luminescence of different materials with LiF.

FIG. 1 and its inset shows the comparative voltage-current and voltage-luminescence characteristics of the devices containing lithium fluoride, unsubstituted quinolate and substituted quinolates as electron injecting layer. It can be seen from the figure that the devices having substituted quinolates as electron injecting layer shows better current and luminescence then the device with lithiumfluoride and unsubstituted quinolate as electron injecting layer.

Figure 2:
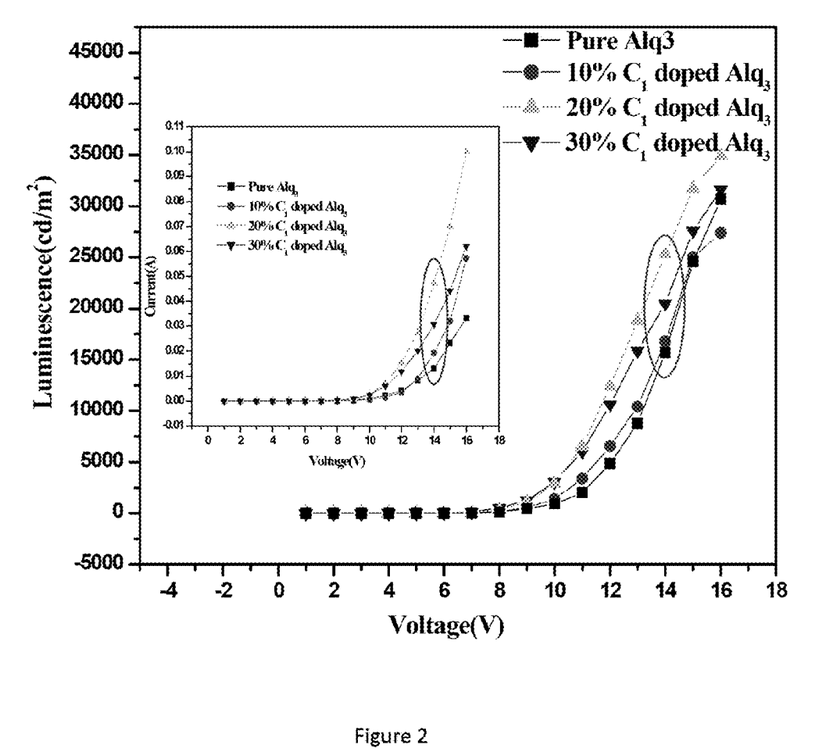
FIGS. 2, 3 and 4 are the graph illustrating comparative voltage v. current and comparative voltage v. luminescence of $C_1$ doped $Alq_3$ with pure $Alq_3$, .$C_2$ doped $Alq_3$ with pure $Alq_3$ and $M_2$ doped $Alq_3$ with pure $Alq_3$ respectively.

FIG. 2 shows the comparative voltage-luminescence characteristics of the devices containing pure Alq$_3$ and doped Alq$_3$ (10%, 20% & 30% LiClq doped) as electron transport material. Inset of the FIG. 2 shows the comparative voltage-current characteristics of the devices consisting pure Alq$_3$ and doped Alq$_3$ (10%, 20% & 30% LiClq doped) as electron transport material. It can be seen from the figure that the devices having LiClq doped layer as ETL shows better current and luminescence then the device with undoped Alq$_3$ as ETL.

Figure 3:
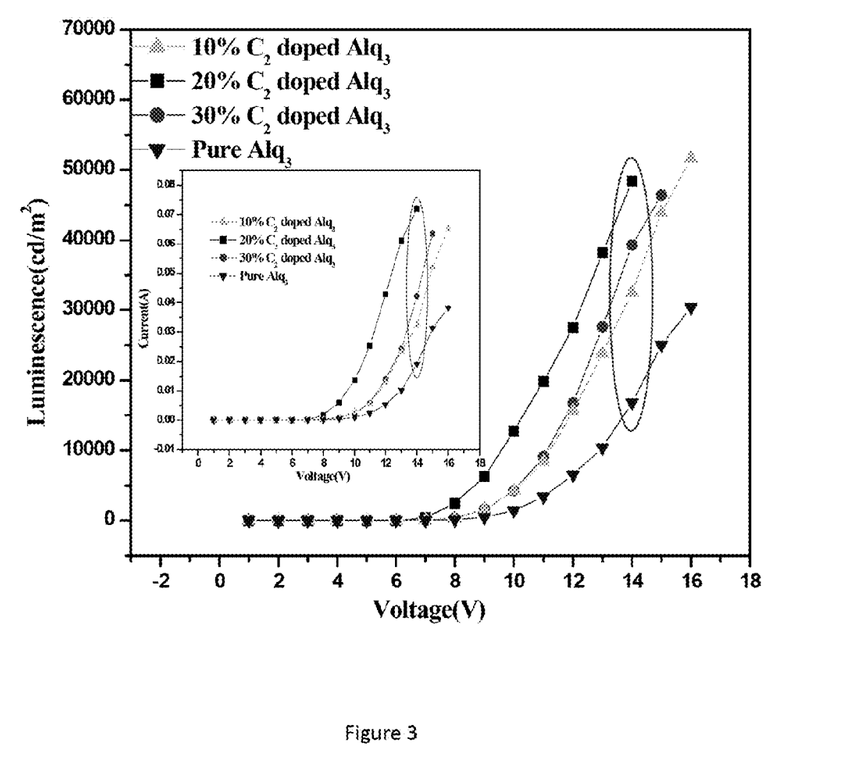

FIG. 3 shows the comparative V-L characteristics of the devices containing pure Alq$_3$ and doped Alq$_3$ (10%, 20% & 30% LiCl$_2$q doped) as electron transport material. Inset of the FIG. 3 shows the comparative V-I characteristics of the devices consisting of pure Alq$_3$ and doped Alq$_3$ (10%, 20% & 30% LiCl$_2$q doped) as electron transport material. It can be seen from the figure that the devices having LiCl$_2$q doped layer as ETL shows better current and luminescence then the device have undoped Alq$_3$ as ETL.

Figure 4:
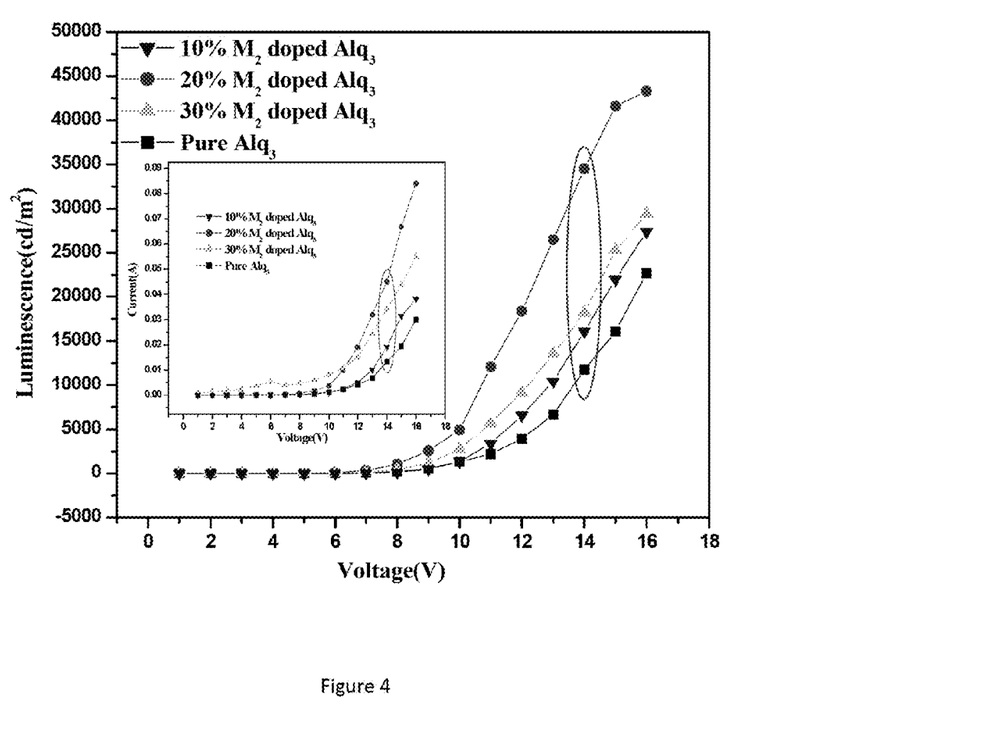

The comparative voltage-luminescence characteristics of the devices containing pure Alq$_3$ and doped Alq$_3$ (10%, 20% & 30% LiMeq doped) as electron transport material are shown in FIG. 4. Inset of the FIG. 4 presents the comparative voltage-current characteristics of the devices have pure Alq$_3$ and doped Alq$_3$ (10%, 20% & 30% LiMeq doped) as electron transport material. It can be inferred from the figure that the devices having LiMeq doped layer as ETL shows better current and luminescence then the device have undoped Alq$_3$ as ETL.

Figure 5:
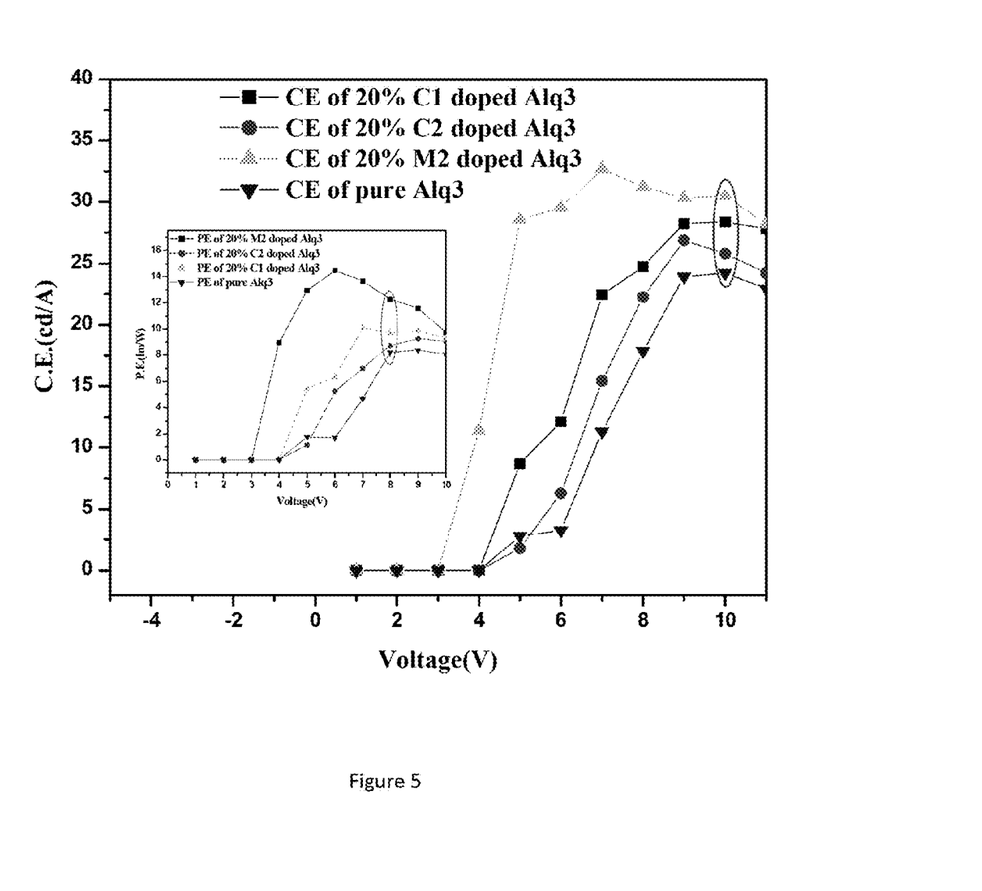
FIG. 5 is a graph illustrating current efficiency v. voltage of the 20% $Alq_3$ doped with different materials with pure $Alq_3$.
Figure 6:
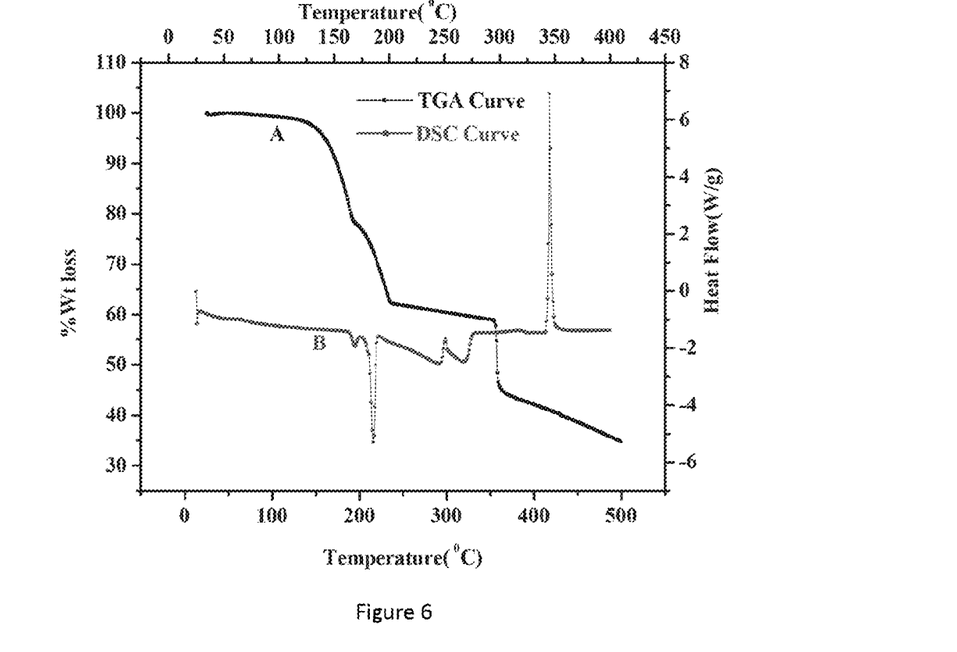
FIGS. 6, 7 and 8 represents TGA-DSC trace of Compound 1, 3 and 5 respectively.
Figure 7:
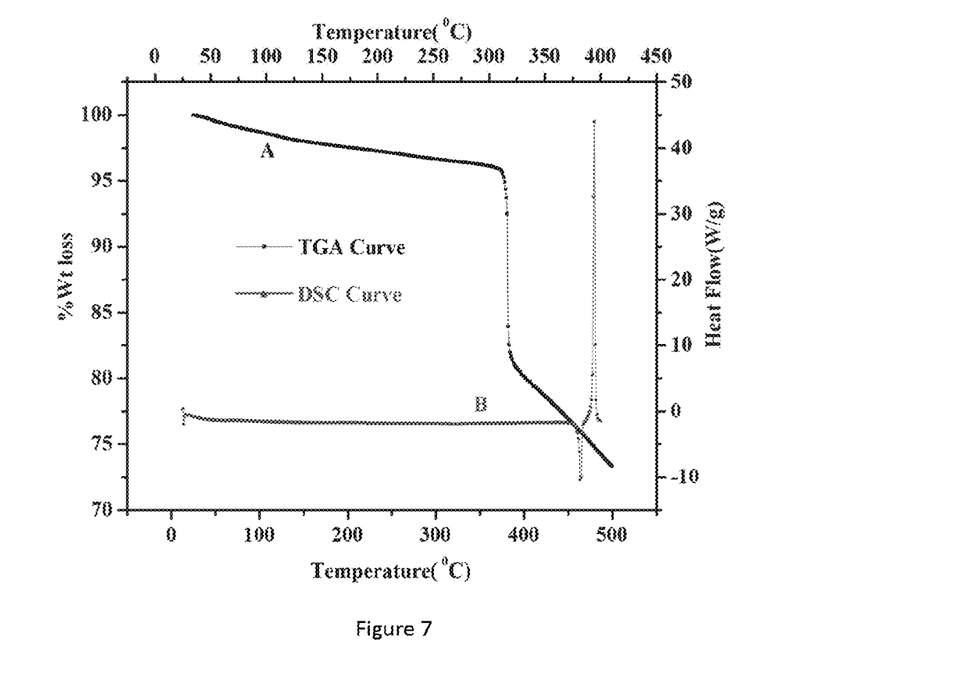
Figure 8:
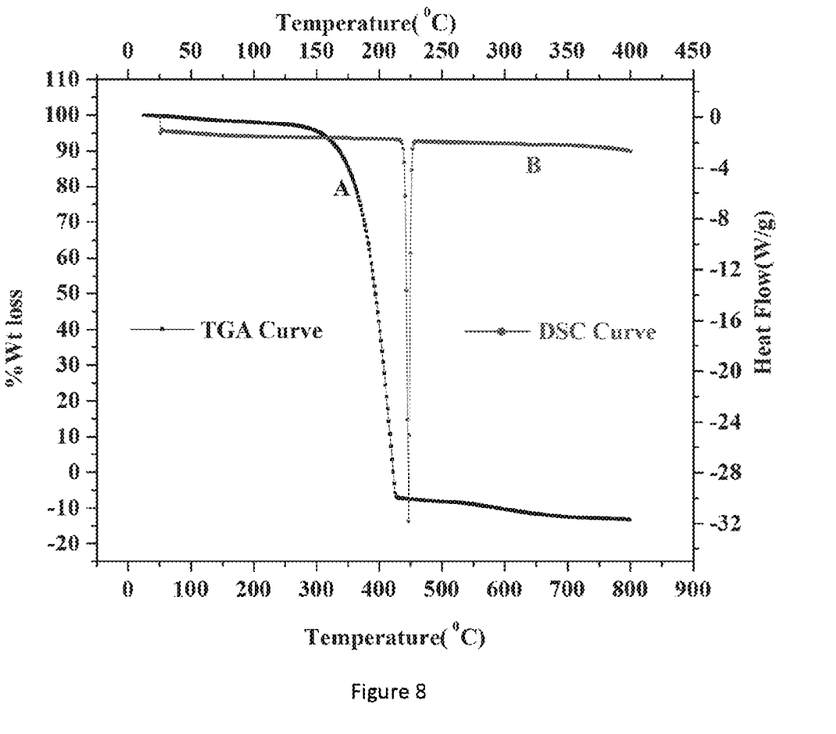

FIG. 5 shows the current efficiency-voltage characteristics of the devices containing pure Alq$_3$ and 20% doped Alq$_3$ (LiClq, LiCl$_2$q and LiMe$_2$q doped) as electron transport material. Inset of the FIG. 5 shows power efficiency-voltage characteristics of the devices containing pure Alq$_3$ and 20% doped Alq$_3$ (LiClq, LiCl$_2$q and LiMe$_2$q doped) as electron transport material. It can be seen from the figure that the devices having doped layer as ETL shows better current and power efficiency then the device have undoped Alq$_3$ as ETL.

EXAMPLES

The following examples are given by way of illustration therefore should not be construed to limit the scope of the present invention.

Example 1

Preparation of lithium 8-hydroxyquinolate Li(C$_9$H$_6$ON) (Compound 1)

8-hydroxyquinoline (1 g, 6.888 mmol) was dissolved in acetonitrile and fresh scratched lithium metal (0.0478 g, 6.888 mmol) was added with continuous stirring of reaction mixture on magnetic stirrer for a period of 25 min. The off white solid so obtained was filtered and dried in vacuum. The yield of the compound was 95%.

Example 2

Preparation of lithium 5-chloro-8-hydroxyquinolate Li($C_9H_5$ClON) (Compound 2 or $Cl_1$)

5-chloro-8-hydroxyquinoline (1 g, 5.6 mmol) was dissolved in acetonitrile and fresh scratched lithium metal (0.0386 g, 5.6 mmol) was added with continuous stirring of reaction mixture on magnetic stirrer for a period of 25 min. The off white solid so obtained was filtered and dried in vacuum. The yield of the compound was 94%.

Example 3

Preparation of lithium 5,7-dichloro-8-hydroxyquinolate Li($C_9H_4Cl_2$ON) (Compound 3 or $Cl_2$)

5,7-dichloro-8-hydroxyquinoline (1 g, 4.695 mmol) was dissolved in acetonitrile and fresh scratched lithium metal (0.032 g, 4.695 mmol) was added with continuous stirring of reaction mixture on magnetic stirrer for a period of 25 min. The off white solid so obtained was filtered and dried in vacuum. The yield of the compound was 93.2%.

Example 4

Preparation of lithium 2-methyl-8-hydroxyquinolate Li($C_{10}H_8$ON) (Compound 4)

2-methyl-8-hydroxyquinoline (1 g, 6.289 mmol) was dissolved in acetonitrile and fresh scratched lithium metal (0.0433 g, 6.289 mmol) was added with continuous stirring of reaction mixture on magnetic stirrer for a period of 25 min. The off white solid so obtained was filtered and dried in vacuum. The yield of the compound was 93.5%.

Example 5

Preparation of lithium 5,7-dimethyl-8-hydroxyquinolate Li($C_{11}H_{10}$ON) (Compound 5 or $M_2$)

5,7-dimethyl-8-hydroxyquinoline (1 g, 5.78 mmol) was dissolved in acetonitrile and fresh scratched lithium metal (0.0398 g, 5.78 mmol) was added with continuous stirring of reaction mixture on magnetic stirrer for a period of 25 min. The off white solid so obtained was filtered and dried in vacuum. The yield of the compound was 93.8%.

Example 6

Preparation of lithium 2-methyloxy-8-hydroxyquinolate Li($C_{10}H_8O_2$N) (Compound 6)

2-methyl-8-hydroxyquinoline (1 g, 5.77 mmol) was dissolved in acetonitrile and fresh scratched lithium metal (0.0396 g, 5.77 mmol) was added with continuous stirring of reaction mixture on magnetic stirrer for a period of 25 min. The off white solid so obtained was filtered and dried in vacuum. The yield of the compound was 91.4%.

Example 7

Preparation of sodium 8-hydroxyquinolate Na($C_9H_6$ON) (Compound 7)

8-hydroxyquinoline (1 g, 6.888 mmol) was dissolved in acetonitrile and fresh sodium metal (0.158 g, 6.888 mmol) was added with continuous stirring of reaction mixture on magnetic stirrer for a period of 25 min. The off white solid so obtained was filtered and dried in vacuum. The yield of the compound was 94%.

Example 8

Preparation of potassium 8-hydroxyquinolate K($C_9H_6$ON) (Compound 8)

8-hydroxyquinoline (1 g, 6.888 mmol) was dissolved in acetonitrile and fresh potassium metal (0.276 g, 6.888 mmol) was added with continuous stirring of reaction mixture on magnetic stirrer for a period of 25 min. The off white solid so obtained was filtered and dried in vacuum. The yield of the compound was 93.4%.

Example 9

Devices were prepared by using 5-chloro-8-hydroxyquinolinatolithium ($Cl_1$ or Compound 2) as electron injecting material having structure ITO/α-NPD(30 nm)/$Alq_3$(35 nm)/$Cl_1$(Xnm)/Al compared with standard device having LiF as electron injecting layer. (i) 1 nm LiF layer as EIL, (ii) 1 nm $Cl_1$ layer as EIL, (iii) 1.8 nm $Cl_1$ layer as EIL. Organic light emitting devices were fabricated on about 120 nm ITO coated glass substrate having sheet resistance of about 20 ohm/area. Substrates were cleaned solvents and then cleaned by plasma treatment. After cleaning, substrates were immediately loaded into a vacuum evaporation system operating at a base pressure of about $10^{-5}$ Torr. Different organic layers were deposited one over the other as per requirement. In three separate devices, $Cl_1$ (X=1 nm and 1.8 nm) is used as EIL and compared with 1 nm LiF layer as EIL. Then a thick layer of Aluminum was deposited through a shadow mask. The device active area was 4 mm by 4 mm.

Example 10

Devices (FIG. 9) were prepared by using 5,7-dichloro-8-hydroxyquinolinatolithium ($Cl_2$ or Compound 3) as electron injecting material having structure ITO/α-NPD(30 nm)/$Alq_3$ (35 nm)/$Cl_2$(Xnm)/Al compared with standard device having LiF as electron injecting layer. (i) 1 nm LiF layer as EIL, (ii) 1 nm $Cl_2$ layer as EIL, (iii) 1.8 nm $Cl_2$ layer as EIL. Organic light emitting devices were fabricated on about 120 nm ITO coated glass substrate having sheet resistance of about 20 ohm/area. Substrates were cleaned solvents and then cleaned by plasma treatment. After cleaning, substrates were immediately loaded into a vacuum evaporation system operating at a base pressure of about $10^{-5}$ Torr.

Figure 9:
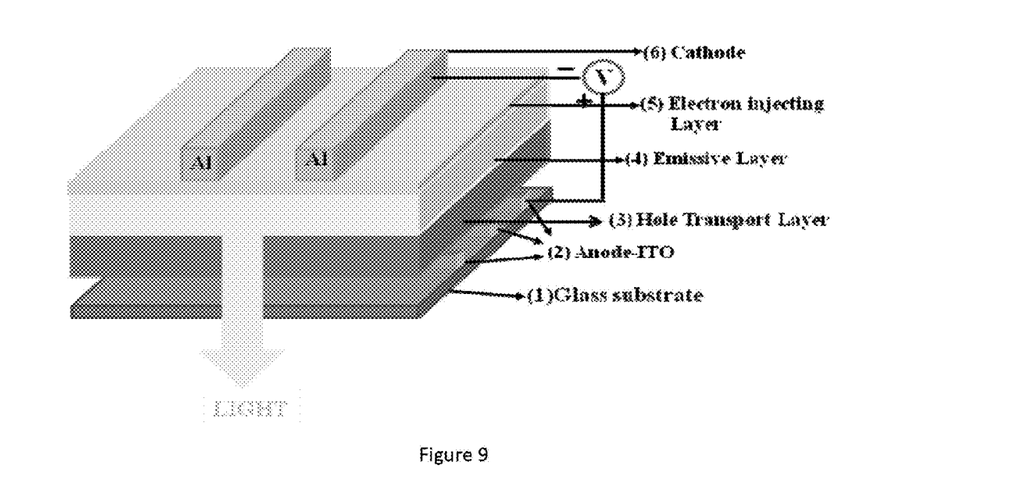
FIG. 9 represents device in which substituted metal quinolated are used as an electron injecting materials.

The device consist of indium tin oxide (ITO) as anode material, a hole transport layer (HTL) of N,N-diphenyl-N,N-bis(1-naphthyl)-1,1-biphenyl-4,4-diamine (α-NPD) and emissive layer of aluminum tris-8-hydroxy quinoline ($Alq_3$) as emissive layer (EML), substituted metal quinolates as electron injection layer (HIL) and aluminum metal as cathode.

Different organic layers were deposited one over the other as per requirement. In three separate devices, Cl$_2$ (X=1 nm and 1.8 nm) is used as EIL and compared with 1 nm LiF layer as EIL. Then a thick layer of Aluminum was deposited through a shadow mask. The device active area was 4 mm by 4 mm.

Example 11

Devices were prepared by using 5,7-dimethyl-8-hydroxyquinolinatolithium (M$_2$ or Compound 5) as electron injecting material having structure ITO/α-NPD(30 nm)/Alq$_3$(35 nm)/M$_2$(Xnm)/Al compared with standard device having LiF as electron injecting layer. (i) 1 nm LiF layer as EIL, (ii) 1 nm M$_2$ layer as EIL, (iii) 1.8 nm M$_2$ layer as EIL. Organic light emitting devices were fabricated on about 120 nm ITO coated glass substrate having sheet resistance of about 20 ohm/area. Substrates were cleaned solvents and then cleaned by plasma treatment. After cleaning, substrates were immediately loaded into a vacuum evaporation system operating at a base pressure of about 10$^{-5}$ Torr. Different organic layers were deposited one over the other as per requirement. In three separate devices, M$_2$ (X=1 nm and 1.8 nm) is used as EIL and compared with 1 nm LiF layer as EIL. Then a thick layer of Aluminum was deposited through a shadow mask. The device active area was 4 mm by 4 mm.

Example 12

Devices were prepared by doping 5-chloro-8-hydroxyquinolinatolithium (Cl$_1$ or Compound 1) in electron transporting layer having structure ITO/α-NPD(30 nm)/5% Ir(ppy)$_3$ in CBP(35 nm)/BCP(6 nm)/X % Cl$_1$ doped Alq$_3$(28 nm)/LiF(1 nm)/Al compared with standard device having undoped Alq$_3$ as electron transporting layer ITO/α-NPD(30 nm)/5% Ir(ppy)$_3$ in CBP(35 nm)/BCP(6 nm)/Alq$_3$(28 nm)/LiF(1 nm)/Al. (i) 10% Cl$_1$ doped Alq$_3$ as ETL, (ii) 20% Cl$_1$ doped Alq$_3$ as ETL, (iii) 30% Cl$_1$ doped Alq$_3$ as ETL. Organic light emitting devices were fabricated on about 120 nm ITO coated glass substrate having sheet resistance of about 20 ohm/area. Substrates were cleaned solvents and then cleaned by plasma treatment. After cleaning, substrates were immediately loaded into a vacuum evaporation system operating at a base pressure of about 10$^{-5}$ Torr.

300 Å of N,N-diphenyl-N,N-bis(1-naphthyl)-1,1-biphenyl-4,4-diamine (α-NPD) as the hole transporting layer; 350 Å of the (8%) Ir(ppy)$_3$ doped in 4,4'-biscarbazolylbiphenyl (CBP) as the emitting layer; 60 Å of 2,9-dimethyl 4,7-diphenyl-1,10-phenanthroline (BCP) as a hole and exciton blocking layer (HBL), 280 Å of tris(8-hydroxyquinolinato)aluminum (Alq$_3$) as electron transport layer and a cathode comprised of 10 Å lithium fluoride and 1000 Å aluminum were sequentially deposited onto the substrate to complete the device structure.

In three separate devices, using Cl$_1$ doped Alq$_3$ (X=10%, 20% and 30%) is used as ETL and compared with Pure Alq$_3$ layer as ETL. Then a thick layer of Aluminum was deposited through a shadow mask. The device active area was 4 mm by 4 mm.

Example 13

Devices (FIG. 10) were prepared by doping 5,7-dichloro-8-hydroxyquinolinatolithium (Cl$_2$ or Compound 3) in electron transporting layer having structure ITO/α-NPD(30 nm)/5% Ir(ppy)$_3$ in CBP(35 nm)/BCP(6 nm)/X % Cl$_2$ doped Alq$_3$ (28 nm)/LiF(1 nm)/Al compared with standard device having undoped Alq$_3$ as electron transporting layer ITO/α-NPD(30 nm)/5% Ir(ppy)$_3$ in CBP(35 nm)/BCP(6 nm)/Alq$_3$(28 nm)/LiF(1 nm)/Al. (i) 10% Cl$_2$ doped Alq$_3$ as ETL, (ii) 20% Cl$_2$ doped Alq$_3$ as ETL, (iii) 30% Cl$_2$ doped Alq$_3$ as ETL. Organic light emitting devices were fabricated on about 120 nm ITO coated glass substrate having sheet resistance of about 20 ohm/area. Substrates were cleaned solvents and then cleaned by plasma treatment. After cleaning, substrates were immediately loaded into a vacuum evaporation system operating at a base pressure of about 10$^{-5}$ Torr. Different organic layers were deposited one over the other as per requirement. In three separate devices, using Cl$_2$ doped Alq$_3$ (X=10%, 20% and 30%) is used as ETL and compared with Pure Alq$_3$ layer as ETL. Then a thick layer of Aluminum was deposited through a shadow mask. The device active area was 4 mm by 4 mm.

Figure 10:
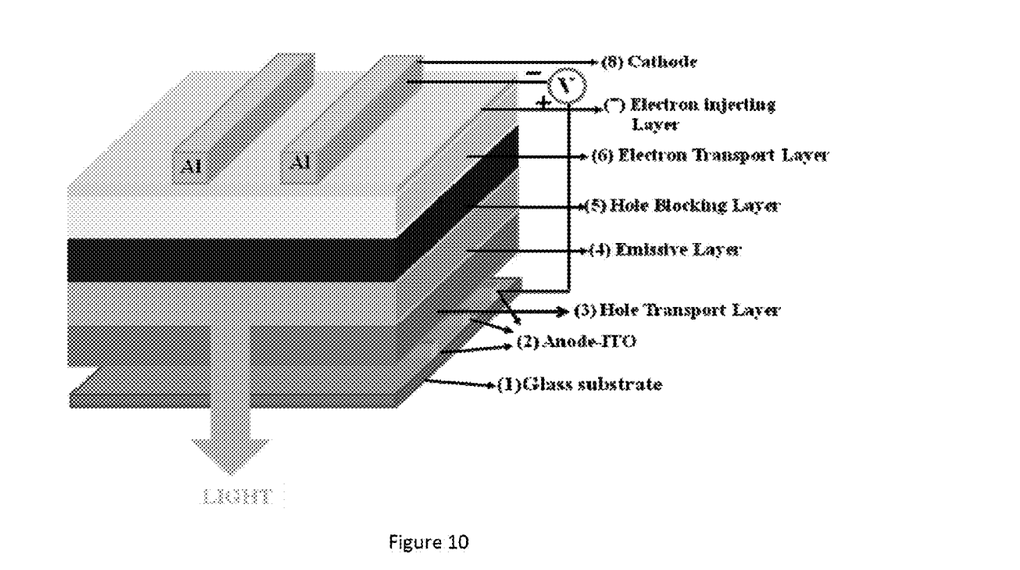
FIG. 10 represents in which substituted metal quinolated are used as n-type dopants in electron transport layer.

The device consist of ITO is indium tin oxide as anode material, α-NPD is, N-diphenyl-N,N-bis(1-naphthyl)-1,1-biphenyl-4,4-diamine as Hole Transport Layer (HTL), Ir(ppy)$_3$-tris(2-phenylpridine) iridium doped in CBP-4,4'-N,N'-dicarbazole-biphenyl is as emissive layer (EML), BCP-2,9-dimethyl-4,7-diphenyl-1,10-phenanthroline as hole blocking layer (HBL)

Substituted quinolates doped in Alq$_3$ is aluminum tris-8-hydroxy quinoline as electron transport later(ETL), Lithium fluoride as electron injection layer (HIL) and aluminum metal as cathode.

Example 14

Devices were prepared by doping 5,7-dimethyl-8-hydroxyquinolinatolithium (M$_2$ or Compound 5) in electron transporting layer having structure ITO/α-NPD(30 nm)/5% Ir(ppy)$_3$ in CBP(35 nm)/BCP(6 nm)/X % M$_2$ doped Alq$_3$(28 nm)/LiF(1 nm)/Al compared with standard device having undoped Alq$_3$ as electron transporting layer ITO/α-NPD(30 nm)/5% Ir(ppy)$_3$ in CBP(35 nm)/BCP(6 nm)/Alq$_3$(28 nm)/LiF(1 nm)/Al. (i) 10% M$_2$ doped Alq$_3$ as ETL, (ii) 20% M$_2$ doped Alq$_3$ as ETL, (iii) 30% M$_2$ doped Alq$_3$ as ETL. Organic light emitting devices were fabricated on about 120 nm ITO coated glass substrate having sheet resistance of about 20 ohm/area. Substrates were cleaned solvents and then cleaned by plasma treatment. After cleaning, substrates were immediately loaded into a vacuum evaporation system operating at a base pressure of about 10$^{-5}$ Torr. Different organic layers were deposited one over the other as per requirement. In three separate devices, using M$_2$ doped Alq$_3$ (X=10%, 20% and 30%) is used as ETL and compared with Pure Alq$_3$ layer as ETL. Then a thick layer of Aluminum was deposited through a shadow mask. The device active area was 4 mm by 4 mm.

Characterization of Cl or Compound 2
C H N Analysis:

The C, H, N analysis of the complex indicated the formula of the complex to be 5-chloro-8-hydroxyquinolinatolithium (I) (C$_9$H$_5$ClNOLi) (found: C, 58.17; H, 2.76; N, 7.62; calc.: C, 58.21; H, 2.69; N, 7.54%)

$^1$H NMR

The $^1$H NMR spectral studies of the LiClq showed that the peaks for aromatic hydrogens were present at 6.96(s 1H), 7.621(s 1H), 7.727(s 1H), 8.413(s 1H) and 8.89(s 1H). The singlet peak due to hydroxyl proton at 8.2(s 1H) (which is present in 5-chloro-8-hydroxyquinoline) was not available in the $^1$H NMR spectra of the complex which confirmed the formation of the complex. The results showed that the peaks shifted significantly downfield against the $^1$H NMR peaks values of the ligand itself, taken from literature indicated the formation of the reported complex.

FT-IR Analysis

The infra-red spectrum of 5-chloro-8-hydroxyquinoline (unreacted ligand) molecule showed a broad characteristic peak at 3241 cm$^{-1}$ corresponding to OH stretching vibration u$_{(O-H)}$ which was absent in the IR spectra of 5-chloro-8-hydroxyquinolinolatolithium which confirmed the formation of Li—O bond. The peak centered at 3070 cm$^{-1}$ is attributed to the stretching vibration at of C—H bond in aromatic ring. Other vibrational modes at 1686 cm$^{-1}$ and 1623 cm$^{-1}$ are assigned to the skeleton stretching vibration of C=C bond in aromatic ring. The peak at 1605 cm$^{-1}$ is attributed to the stretching vibration of C=N bond. The vibrational absorption peak of C—O at 1237 cm$^{-1}$ is weak and narrow. The characteristic peaks of quinolinic rings from 600 cm$^{-1}$ to 800 cm$^{-1}$ showed the existence of quinolinic rings. Hence the complex formation occurred successfully and confirmed finally the structure to be a 5-chloro-8-hydroxyquinolinolato lithium(I).

TGA and DSC

Thermo-gravimetric analysis (TGA; Mettler Toledo TGA/SDTA 851e Instruments, DSC; Mettler Toledo DSC 822e) of the samples were carried out at a heating rate of 10° C.min$^{-1}$ in nitrogen atmosphere. The TGA-DSC traces of complexes are shown in FIGS. 3.7-3.11) and are explained as follows.

Curve A of FIG. 3.8 corresponds to TGA of LiClq in nitrogen atmosphere. It can be seen from the TGA data that complex exhibited good thermal stability. The onset temperature of weight loss was 180° C. and 21% weight loss occurred at 190° C. At 350° C. the complex lost complete weight and decomposed completely.

Thermally induced phase transition behavior of LiClq was investigated by DSC under nitrogen atmosphere. Curve B of FIG. 3.8 shows the DSC curve of LiClq. DSC curve revealed that the LiClq was amorphous upto 170° C. because its temperature of crystallization was at 175° C. On heating upto 170° C., no crystallization and melting were observed.

Characterization of C2 or Compound 3

C H N Analysis

The C, H, N analysis of the complex indicated the formula of the complex to be 5,7-dichloro-8-hydroxyquinolinolatolithium (I) (C$_9$H$_4$Cl$_2$NOLi) (found: C, 49.03; H, 1.96; N, 6.28; calc.: C, 49.10; H, 1.82; N, 6.36%)

$^1$H NMR

The $^1$H NMR spectral studies of the LiCl$_2$q showed that the peaks for aromatic hydrogens were present at 7.42(s 1H), 7.51(s 1H), 8.372(s 1H) and 8.828(s 1H). The singlet peak due to hydroxyl proton at 7.26(s 1H) (which is present in 5,7-chloro-8-hydroxyquinoline) was absent in the $^1$H NMR spectra of the complex and confirmed the formation of the complex. The results showed that the peaks shifted significantly downfield against the $^1$H NMR peaks values of the ligand itself, taken from literature indicated the formation of the reported complex.

FTIR Analysis

The infra-red spectrum of 5,7-dichloro-8-hydroxyquinoline(unreacted ligand) molecule showed a broad characteristic peak at 3076 cm$^{-1}$ corresponding to OH stretching vibration u$_{(O-H)}$ which was absent in the IR spectra of 5,7-dichloro-8-hydroxyquinolinolatolithium confirms the formation of Li—O bond. The peak centered at 3076 cm$^{-1}$ is attributed to the stretching vibration at of C—H bond in aromatic ring. Other vibrational modes at 1613 cm$^{-1}$ and 1582 cm$^{-1}$ are assigned to the skeleton stretching vibration of C=C bond in aromatic ring. The peak at 1659 cm$^{-1}$ is attributed to the stretching vibration of C=N bond. The vibrational absorption peak of C—O at 1266 cm$^{-1}$ is weak and narrow. The characteristic peaks of quinolinic rings from 600 cm$^{-1}$ to 800 cm$^{-1}$ showed the existence of quinolinic rings. Hence the complex formation occurred successfully and confirmed finally the structure to be a 5,7-dichloro-8-hydroxyquinolinolatolithium(I).

TGA and DSC

Curve A of FIG. 3.9 shows TGA of LiCl$_2$q in nitrogen atmosphere. It is evident from the TGA data that complex exhibited excellent thermal stability. The onset temperature of weight loss was 350° C. and 18% weight loss was occurred at 360° C. At 500° C. the complex lost total weight and decomposed completely.

Thermally induced phase transition behavior of LiCl$_2$q was investigated by DSC under nitrogen atmosphere. Curve B of FIG. 3.9 shows the DSC curve of LiCl$_2$q. DSC curve revealed that the LiCl$_2$q was amorphous upto 340° C. because its temperature of crystallization was at 340° C. On heating upto 340° C., no crystallization and melting were observed.

Characterization of M2 Compound 5

C H N Analysis

The C, H, N analysis of the complex indicated the formula of the complex to be 5,7-dimethyl-8-hydroxyquinolinolatolithium (I) (C$_{11}$H$_{10}$NOLi) (found: C, 73.63; H, 5.64; N, 7.78; calc.: C, 73.68; H, 5.58; N, 7.81%)

$^1$H NMR

The $^1$H NMR spectral studies of the LiMe$_2$q showed that the peaks for aromatic hydrogens were present at 2.52(m 3H), 3.62(m 3H), 6.99(s 1H), 7.12 (s 1H), 7.27(s 1H), and 8.05(s 1H). The singlet peak due to hydroxyl proton at 8.19(s 1H) (which is present in 5,7-dimethyl-8-hydroxyquinoline) was found absent in the $^1$H NMR spectra of the complex, which showed the formation of the complex. The results showed that the peaks shifted significantly downfield against the $^1$H NMR peaks values of the ligand itself, taken from literature indicated the formation of the reported complex.

FTIR Analysis

The infra-red spectrum of 5,7-dimethyl-8-hydroxyquinoline (unreacted ligand) molecule showed a broad characteristic peak at 3012 cm$^{-1}$ corresponding to OH stretching vibration u$_{(O-H)}$ which was found absent in the IR spectra of 5,7-dimethyl-8-hydroxyquinolinolatolithium confirms the formation of Li—O bond. The peak centered at 3017 cm$^{-1}$ is attributed to the stretching vibration at of C—H bond in aromatic ring. Other vibrational modes at 1664 cm$^{-1}$ and 1677 cm$^{-1}$ are assigned to the skeleton stretching vibration of C=C bond in aromatic ring. The peak at 1617 cm$^{-1}$ is attributed to the stretching vibration of C=N bond. The vibrational absorption peaks of C—O at 1236 cm$^{-1}$ is weak and narrow. The characteristic peaks of quinolinic rings from 600 cm$^{-1}$ to 800 cm$^{-1}$ showed the existence of quinolinic rings. Hence the complex formation occurred successfully and confirmed finally the structure to be a 5,7-dimethyl-8-hydroxyquinolinolato lithium(I).

TGA and DSC

Curve A of FIG. 3.11 is the TGA curve of LiMe$_2$q in nitrogen atmosphere at a heating rate of 10° C. min$^{-1}$. It can be seen from the TGA data that complex exhibited excellent thermal stability. The onset temperature of weight loss was 300° C., and temperature for 20% weight loss was 310° C. At 412° C. the complex lost all of its weight and decomposed completely.

Thermally induced phase transition behavior of LiMe$_2$q was investigated by DSC under nitrogen atmosphere. Curve B of FIG. 3.11 shows the DSC curve of LiMe$_2$q. DSC curve revealed that the LiMe$_2$q was amorphous upto 225° C., because its temperature of crystallization was at 230° C. On heating upto 225° C., no crystallization and melting were observed.

TGA-DSC data of the complexes shows that these complexes (Compound 1, 3 and 5) have high thermal stability and high crystallization temperature. Such amorphous materials are particularly favored for OLEDs because aggregation and crystallization will affect the device stability and lifetime.

| Photo-physical properties of lithium metal complexes | | | |
|---|---|---|---|
| | UV-vis absorption | | PL |
| Complex | $\pi \to \pi^*$, $\lambda_{max}$ (nm) | $n\text{-}\pi^*$, $\lambda_{max}$ (nm) | $\lambda_{max}$ (nm) |
| C1 or Compound 2 | 326 | 373 | 484 |
| C2 or Compound 3 | 324 | 364 | 480 |
| M2 or Compound 5 | 330 | 379 | 511 |

Advantages of the Invention

The present invention provides easy and fast method for the preparation of lithium metal quinolates.

In this method, alkyllithium as a reactant is not requiring for the synthesis, which is itself quite difficult to prepare.

This method is less time taking and hence minimizes the reaction time.

With this method, we can synthesize substituted metal quinolates and quinolates of other metals like sodium, potassium.

The reaction yield in this method is also very good in the range of 90-95%.

A highly injecting contact can be obtained with substituted quinolates which can be uniformly deposited with in a range of thickness unlike LiF layer which become an insulator above a thickness of 1 nm.

Careful handling of the reactive metals is not required which are usually used to enhance the electron injection in an organic semiconductor based devices.

Efficient charge balance in organic light emitting devices can be achieved with substituted metal quinolates in electron transport layer.

We claim:

1. A process for the preparation of compound of general formula 1

General Formula 1 wherein

M is Lithium, sodium or potassium;

each R is independently H, alkyl, alkoxy, aryl, aryloxy, amino, amido or halogen, the process comprising the steps of:
  i. dissolving substituted 8-hydroxyquinoline of formula X and fresh scratched metal in 1:1 molar ratio in polar solvent with continuous stirring for period in the range of 20 to 25 min to obtain a solution Formula X wherein each R is independently H, alkyl, alkoxy, aryl, aryloxy, amino, amido or halogen; and
  ii. filtering the solution as obtained in step (i), drying in vacuum at temperature in the range of 100 to 120° C. for period in the range of 10 to 12 hrs followed by purification by vacuum sublimation to obtain pure compound of general formula 1.

2. The process according to claim 1, wherein the metal used in step (i) is lithium, sodium or potassium.

3. The process according to claim 1, wherein the polar solvent used in step (i) is acetonitrile, methanol, ethanol, propanol, or dichloromethane.

4. The process according to claim 1, wherein the yield of compound of general formula 1 is in the range of 90 to 95%.

5. The process according to claim 1, wherein the compound of general formula 1 is one of the following compounds:

Compound 1

Compound 2

Compound 3

Compound 4

6. The process according to claim 4, wherein the compound of general formula 1 is one of the following compounds:

7. A method for preparing an organic light emitting device, the method comprising forming, among other layers, and electron injecting layer by employing a compound of general formula 1 which is prepared by the process of claim 4.

8. A method for an organic light emitting device, the method comprising forming an electron injecting layer by employing a compound of general formula 1 which is prepared by the process of claim 1.

9. The method according to claim 8, wherein the compound of general formula 1 is additionally a n-dopant in an electron transport layer.

10. The method according to claim 9, wherein n-dopants are in the range of 10 to 30% by weight.

11. The method according to claim 8, wherein the electron injecting layer is 1 to 2 nm thick.

12. The method according to claim 8, wherein the organic emissive layer is 30 to 35 nm thick.

13. The method according to claim 8, wherein said organic light emitting device comprises:
  i. a substrate layer;
  ii. an anode layer superimposed on substrate layer;
  iii. a hole transport layer deposited on the anode layer;
  iv. an organic emissive layer covering the hole transport layer;
  v. an electron transport layer covering the organic emissive layer;

vi. an electron injection layer covering the electron transport layer;

vii. a cathode superimposed over the electron injection layer.

14. The method according to claim 13, wherein substrate layer is composed of transparent glass.

15. The method according to claim 13, wherein the anode layer is composed of indium tin oxide.

* * * * *